United States Patent [19]

Berry, Jr.

[11] Patent Number: 5,281,400
[45] Date of Patent: Jan. 25, 1994

[54] PLASTIC AUTOCLAVE TRAY AND LID COMBINATION

[75] Inventor: Bernie B. Berry, Jr., Indianapolis, Ind.

[73] Assignee: Carr Metal Products, Indianapolis, Ind.

[21] Appl. No.: 954,563

[22] Filed: Sep. 30, 1992

[51] Int. Cl.$^5$ ................................................ A61L 2/26
[52] U.S. Cl. ..................... 422/295; 422/102; 422/297; 422/300; 422/310; 206/363; 206/369; 206/370
[58] Field of Search ............... 422/295, 297, 300, 310, 422/104, 102; 220/315, 324; 206/363, 369, 370, 373, 508, 509, 511

[56] References Cited

U.S. PATENT DOCUMENTS

| | | | |
|---|---|---|---|
| 857,240 | 6/1907 | Henning | |
| 1,973,947 | 9/1934 | Enderle | 27/35 |
| 3,179,287 | 4/1965 | Rickmeier, Jr. | 220/94 |
| 3,285,409 | 11/1966 | Loran | 206/63.5 |
| 3,433,269 | 3/1969 | Sackett, Sr. | 138/92 |
| 3,532,221 | 10/1970 | Kaluhiokalani et al. | 211/60 |
| 3,589,511 | 6/1971 | Britt | 206/65 |
| 3,634,937 | 1/1972 | Green | 32/1 |
| 3,890,096 | 6/1975 | Nichol et al. | 21/105 |
| 3,982,630 | 9/1976 | Garnier | 206/369 |
| 3,991,902 | 11/1976 | Ford, Jr. | 220/324 |
| 4,191,291 | 3/1980 | Brown | 206/369 |
| 4,512,498 | 4/1985 | Leibinger | 422/310 X |
| 4,541,992 | 9/1985 | Jerge et al. | 422/300 |
| 4,572,371 | 2/1986 | Asenbauer | 206/443 |
| 4,593,816 | 6/1986 | Langenbeck | 206/508 |
| 4,625,885 | 12/1986 | Nichols | 220/324 |
| 4,643,303 | 2/1987 | Arp et al. | 206/370 |
| 4,661,326 | 4/1987 | Schainholz | 422/310 |
| 4,728,504 | 3/1988 | Nichols | 422/310 |
| 4,774,063 | 9/1988 | Runnells | 422/297 |
| 4,783,321 | 11/1988 | Spence | 422/300 |
| 4,798,292 | 1/1989 | Hauze | 206/439 |
| 4,826,348 | 5/1989 | Brightman | 403/330 |
| 4,852,738 | 8/1989 | Craig et al. | 206/369 |
| 4,854,475 | 8/1989 | Riihimaki et al. | 220/337 |
| 4,892,213 | 1/1990 | Mason, Jr. | 206/508 |
| 4,959,199 | 9/1990 | Brewer | 422/300 |
| 5,002,319 | 3/1991 | Chandler | 292/17 |
| 5,004,418 | 4/1991 | Porteous | 433/77 |
| 5,031,768 | 7/1991 | Fischer | 220/324 |
| 5,084,251 | 1/1992 | Thomas | 422/300 |
| 5,098,676 | 3/1992 | Brooks, Jr. | 422/292 |

Primary Examiner—James C. Housel
Assistant Examiner—Jan M. Ludlow
Attorney, Agent, or Firm—Woodard, Emhardt, Naughton, Moriarty & McNett

[57] ABSTRACT

A plastic autoclave enclosure for retaining and storing medical instruments and apparata which must be autoclaved includes a molded tray, a molded lid and a pair of oppositely disposed slide latches which are used to secure the molded lid to the molded tray. The molded tray has an outwardly extending flange and disposed therein a pair of spaced-apart keyhole slots. The slide latches are attached to opposite ends of the molded lid and include a protruding pin portion from each latch which has an enlarged head and this enlarged head is received by the corresponding keyhole slot. The base of the molded tray is configured with two spaced-apart ribs and the molded lid has a pair of spaced-apart ribs which define the top surface into three generally rectangular areas. The spacing and length dimension of the tray ribs is such that the base of the tray may be stacked onto the top of the lid thereby allowing a plurality of autoclave enclosures to be stacked one on top of the other.

7 Claims, 4 Drawing Sheets

PLASTIC AUTOCLAVE TRAY AND LID COMBINATION

BACKGROUND OF THE INVENTION

The present invention relates in general to plastic autoclave tray enclosures in particular to a plastic autoclave tray and lid combination for medical and dental instruments, appliances, and implant prostheses.

Some of the aspects of importance in the design of autoclave enclosures include handling, opening and storage convenience, weight, compactness, durability and versatility in accepting a variety of holders and retainers for the instruments and appliances. The present invention addresses some of these aspects in a novel manner providing improvements to what heretofore have been available.

Although a majority of autoclave trays and enclosures are fabricated out of metal for durability, strength and versatility reasons, there are modern plastics whose heat resistance enables them to be used for autoclave trays and enclosures. Plastics have certain physical features that are advantageous when compared to metal and weight advantages over metal and provide the ability to easily provide unique styles and shapes for the enclosure which might not be readily producible in metal.

Autoclave trays, cassette and enclosure designs which might be of interest in order to appreciate some of the aspects of the conventional design wisdom are disclosed in the following patents.

| Patent No. | Patentee | Issue Date |
| --- | --- | --- |
| 5,098,676 | Brooks, Jr. | March 24, 1992 |
| 5,002,319 | Chandler | March 26, 1991 |
| 1,973,947 | Enderle | Sept. 18, 1934 |
| 3,433,269 | Sackett, Sr. | March 18, 1969 |
| 4,826,348 | Brightman | May 2, 1989 |
| 3,179,287 | Rickmeier, Jr. | April 20, 1965 |
| 3,091,488 | Vander Sande et al. | May 28, 1963 |
| 805 909 | Külbel-Germany | June 4, 1951 |

Brooks discloses a plastic sterilization and storage container which includes a lower tray portion and an upper lid portion. Disposed within the tray portion is a finger mat for supporting surgical instruments. The tray and lid are molded out of plastic and each includes an outwardly extending flange portion with the lid flange fitting over and around the tray flange. A metal clamp then pivots from the plastic lid over and around the overlapping flanges as a means to clamp the lid onto the tray.

Chandler discloses a sheet metal latch apparatus which may be used to attach a cover or lid portion to a base container.

Enderle discloses a lid and container combination in which a pivoting U-shaped latch is used to clamp together the outwardly extending flanges of both members.

Sackett discloses a rapid access closure system in which a base container is covered by a lid each of which have an outwardly extending flange portion. The two flanges are secured together by a pin arrangement.

Brightman discloses a coupling set for interlocking objects which includes first and second coupling elements each having an integral stud by which it is anchored to one of two objects to be interlocked.

Rickmeier discloses a container and lid in combination each of which includes an outwardly extending flange portion. The lid is provided with a series of slot openings and the base container has a matching series of protruding extensions. A pivotal or swivel latch mechanism is attached to the lid and provides an interlocking arrangement when the lid is secured to the base container.

Vander Sande discloses a rotary latch mechanism for use in securing together a base container and lid member. In this particular arrangement there are no outwardly extending flanges and the rotary latch relies principally on a spring clip and pin arrangement for securing the hinged lid in a closed position on the base container.

The German patent discloses a hinged lid and tray combination including a front wall, two-part latch mechanism. The lid includes an extended pin and the base or tray portion includes a spring clip slot with inwardly protruding projections. The latching mechanism relies on the lid pin pushing through the tray projections and coming to rest at a point of clearance beneath the projections. The projections are spring-biased such that when suitable force is exerted on the lid the pin can be pulled back through the protruding portions in order to open the container.

The plastic autoclave tray and lid combination of the present invention departs from the designs and features of these earlier references by providing a molded plastic, stackable design with a quiet, smooth and convenient latch design.

SUMMARY OF THE INVENTION

A plastic autoclave enclosure according to a typical embodiment of the present invention includes a molded tray having an outwardly extending flange portion and a latch receiving keyhole opening, a molded lid having an outwardly extending flange portion which is larger and shaped similarly to the flange portion of the molded tray so as to fit over and around the flange portion of the molded tray, and a slide latch mechanism attached to the molded lid and designed for securing the lid to the flange portion of the molded tray by means of the latch-receiving opening.

One object of the present invention is to provide an improved plastic autoclave enclosure.

Related objects and advantages of the present invention will be apparent from the following description.

DESCRIPTION OF THE PREFERRED EMBODIMENT

Figure 1:
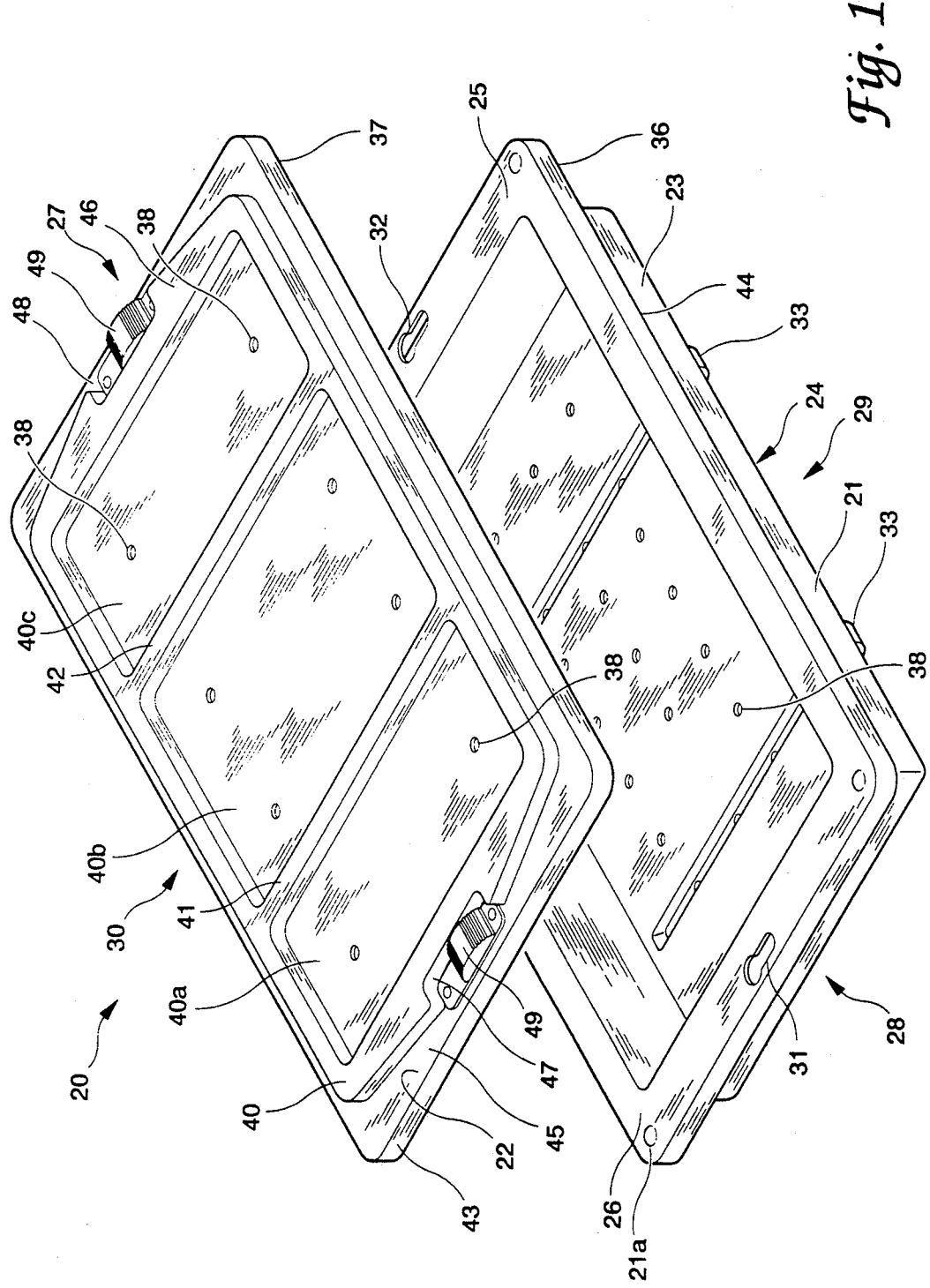
FIG. 1 is a perspective, exploded view of a plastic autoclave enclosure according to a typical embodiment of the present invention.
Figure 2:
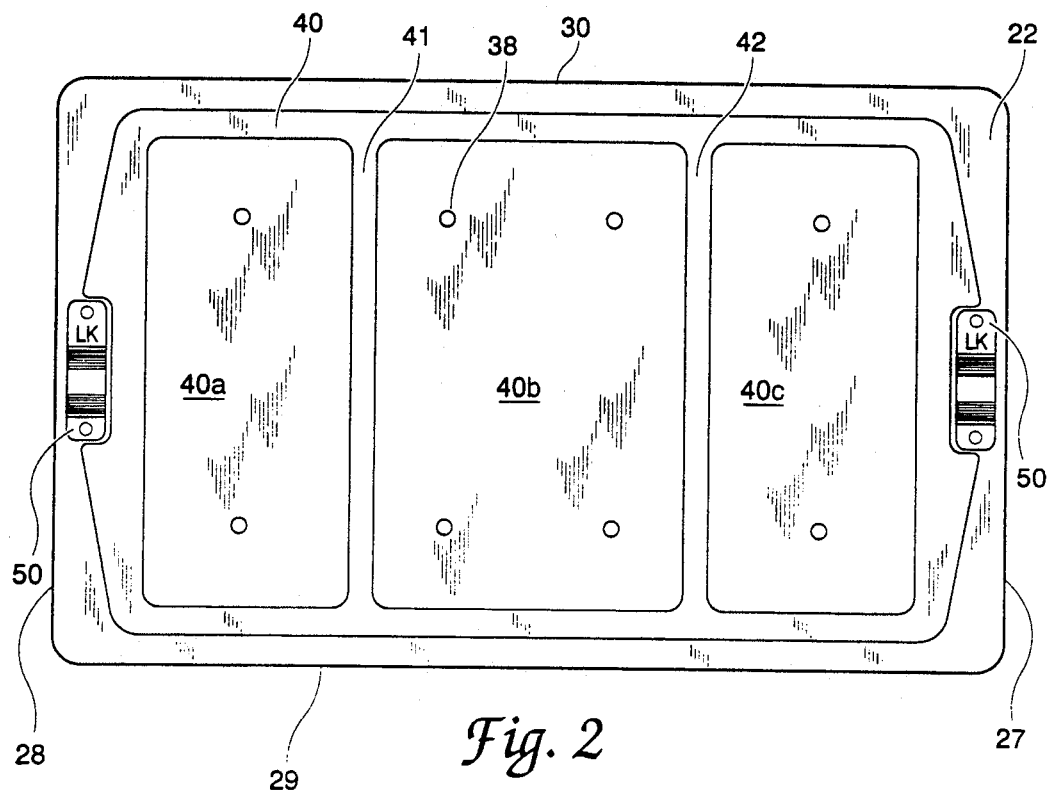
FIG. 2 is a top plan view of the FIG. 1 plastic autoclave enclosure in a closed condition.
Figure 3:
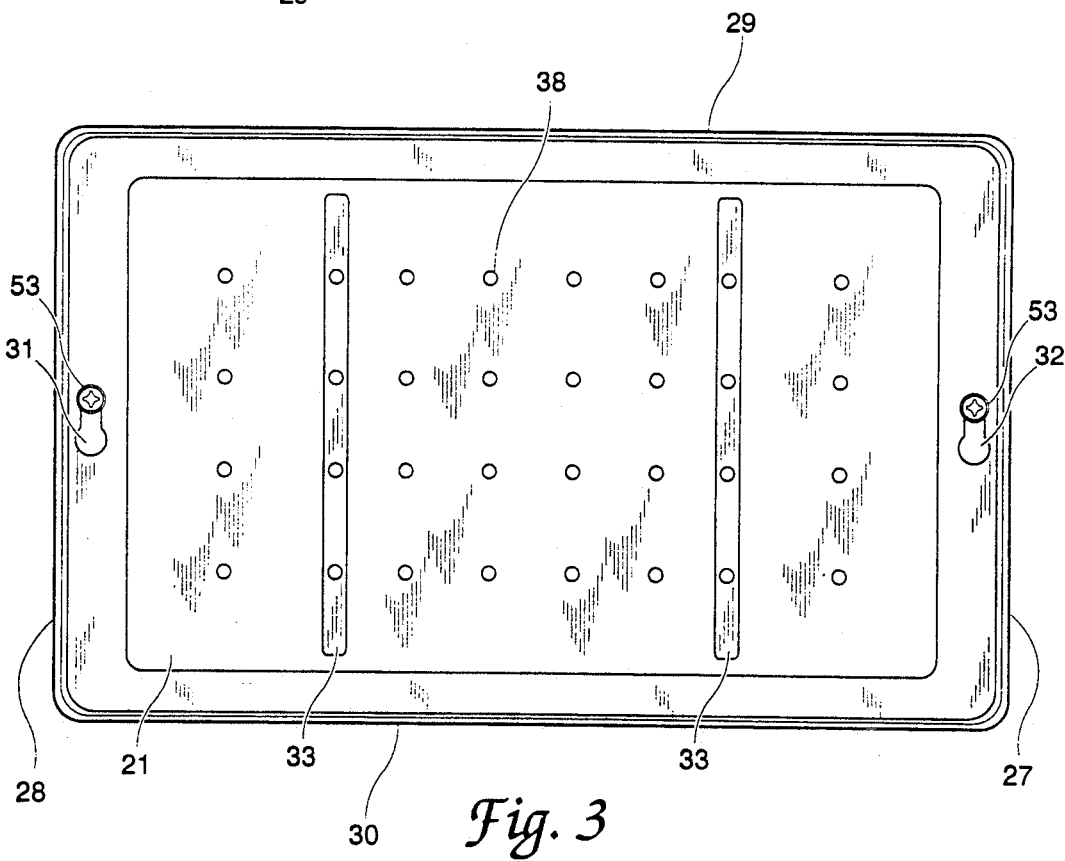
FIG. 3 is a bottom plan view of the FIG. 1 plastic autoclave enclosure in a closed condition.
Figure 4:
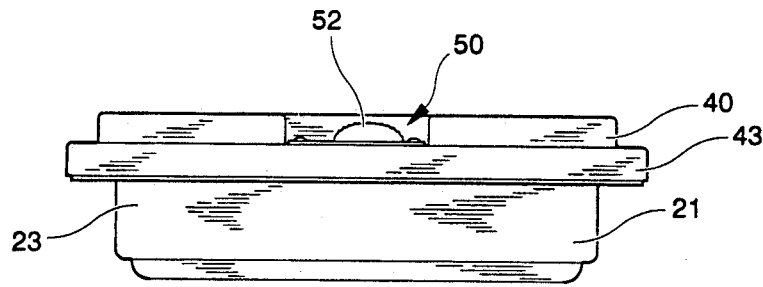
FIG. 4 is a side elevational view of the FIG. 1 plastic autoclave enclosure in a closed condition.
Figure 5:
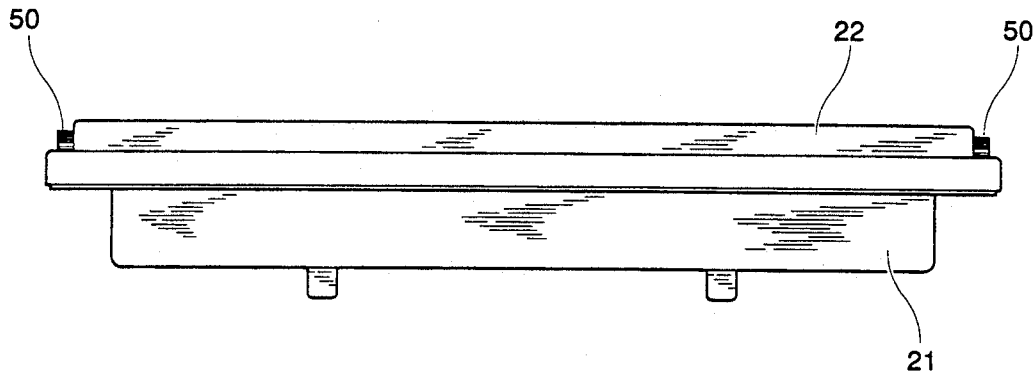
FIG. 5 is a front elevational view of the FIG. 1 plastic autoclave enclosure in a closed condition.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIGS. 1, 2, 3, 4 and 5 the plastic autoclave enclosure 20 including tray 21 and lid 22 according to the Present invention is illustrated. The tray 21 is a molded, vacuum formed, integral and unitary member having a generally rectangular sidewall 23, base 24 and surrounding an outwardly extending rectangular flange 25 (see FIG ,6). Disposed on and as part of flange 25 are four raised protuberances 21a, one centered in each corner of flange 25. While flange 25 has a generally rectangular shape in its top plan orientation, the flange has an inverted U-shaped lateral cross section. The top surface 26 of flange 25 is wider at enclosure ends 27 and 28 than at or along the enclosure sides 29 and 30. This extra width along the enclosure ends provides a sufficient surface area for the placement of keyhole slots 31 and 32 each of which have an enlarged portion at one end and a more narrow slot extending therefrom. It is also to be noted that keyhole slots 31 and 32 have the same orientation such that the narrower slot portion extends from the enlarged opening in the same direction To lock the tray to the lid the slide latches are pulled toward the user, if the user is positioned on enclosure side 29. To release the lid, the slide latches are pushed toward side 30, in the direction of the enlarged opening in each keyhole slot.

Protuberances 21a have a vacuum formed height of approximately 0.065 inches and when the lid 22 is closed onto the tray, these protuberances create a lid to tray separation. In order for the slide latches to operate to secure the lid to the tray, the lid must flex. This flexure induces more pressure on the latching members thereby reducing the necessity for holding tight tolerances in the latching components and the thickness of the lid and tray. The separation crevices which are left between the tray and lid provide additional passageways for sterilant during the autoclaving process.

Vacuum formed into the base 24 of tray 21 are a pair of substantially parallel stiffening and support ribs 33 which additionally serve as feet for the enclosure. Ribs 33 raise base 24 off of whatever the supporting surface may be used and allows drainage of any moisture or condensation which is collected within enclosure 20. All of the inner and outer corners and corner edges of tray 21 and lid 22 are smooth and rounded except for the underside surfaces 36 (tray 21) and 37 (lid 22). The tray and lid are vacuum formed with a pressure flange which is then removed leaving surfaces 36 and 37. While surfaces 36 and 37 are smooth, there is not sufficient thickness in order to provide a large radiused or rounded surface. These surfaces are basically flat though any sharp edges are removed by deburring after the pressure flange is removed. The smooth and rounded corners and edges are readily fabricated as part of enclosure 20 due to the fact that the tray and lid are vacuum formed out of a high temperature plastic. These smooth and rounded inner and outer corners and edges provide an enclosure which is easy and comfortable to handle and to use. The smooth surfaces and rounded edges will not puncture or tear any paper barrier wrapping. A plurality of steam holes 38 are drilled into the tray 21 and lid 22. Suitable materials for the tray 21 and lid 22 include "ULTEM-1000" offered by General Electric and "RADEL 5000" offered by Amoco.

Lid 22 is arranged with an inset, raised frame portion 40 and integrally connected therewith a pair of substantially parallel ribs 41 and 42. These two ribs divide the top surface into three generally rectangular areas 40a, 40b and 40c. The underside of frame portion 40 and ribs 41 and 42 define an open channel network with all channel areas open and interconnected. This raised frame portion design in combination with the two ribs provides added strength and rigidity to lid 22. The lid is able to maintain its substantially flat configuration without warpage or distortion. This in turn assures that the outer lip 43 of lid 22 will fit closely down over and around the outer lip 44 of tray 21.

Figure 6:
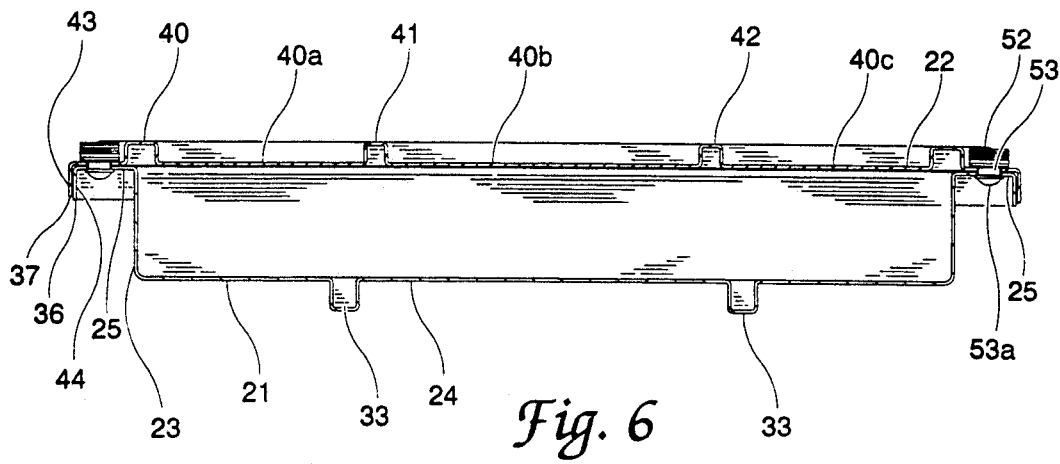
FIG. 6 is a front elevational view in full section of the FIG. 1 plastic autoclave enclosure in a closed condition.
Figure 6A:
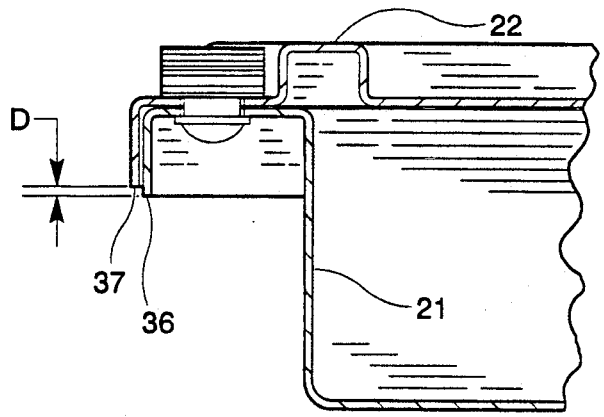
FIG. 6A is an enlarged detail fo the partial side elevational view in full section of the tray and lid offset.

Referring to FIG. 6A the edge offset (D) between the tray (surface 36) and lid (surface 37) is illustrated. In accordance with the present invention the lower edge 37 of the lid flange is trimmed to a dimensional height so as to be shorter than the tray lower edge 36. This construction enables any pick-up, lifting or handling forces to be transmitted to the tray flange and in effect not to the lid flange. The result is a lower or decreased likelihood that the tray contents will be dumped if the latches are inadvertently left open.

Figure 7:
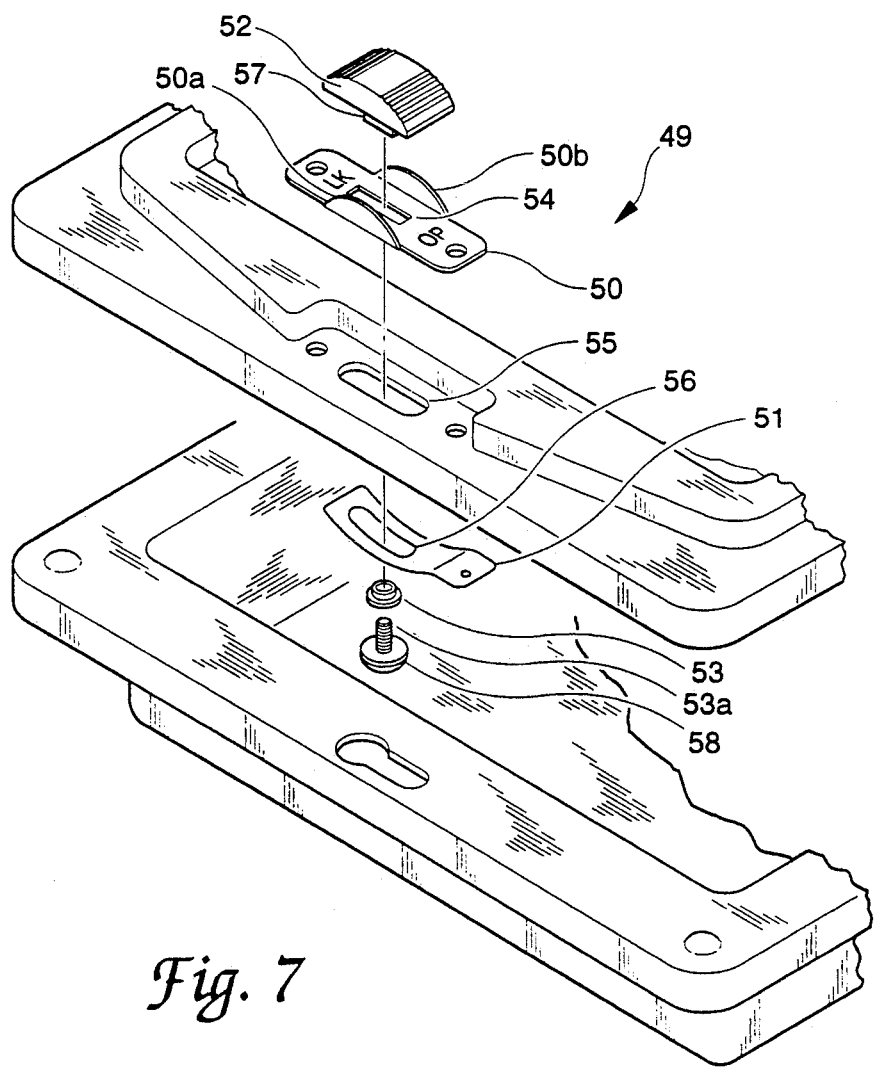
FIG. 7 is an exploded view of the latch mechanism used to secure the lid and tray portions together according to the present invention.

The raised frame portion 40 is notched at ends 45 and 46 with molded relief areas 47 and 48, respectively. Riveted in position within areas 47 and 48 are a pair of slide latches 49 (see FIG. 7). Each slide latch includes a metal frame 50, a convex spring clip 51, a convex slide 52 and shouldered collar 53 and cooperating screw 53a. The assembly of the shouldered collar and the screw creates pin-type member with an enlarged head. Frame 50 is riveted at opposite ends to the top surface of lid 22 and spring clip 51 is riveted at one end to the underside surface lid 22 permitting necessary flexing of the spring. The rectangular slot 54 disposed in frame 50 is aligned with the oblong slot 55 in lid 22 and with the oblong slot 56 in clip 51. Slide 52 has a protruding extension on its underside which extends through slot 54 and slot 55. Shouldered collar 53 abuts up against extension 57 in order to establish a fixed clearance spacing for the head of screw 53a. This insures that the spring clip will not be flattened by over tightening or advancing of screw 53a. The enlarged head 58 of screw 53a is disposed on the back side of spring clip 51 and the reduced diameter portion of collar 53 rides within the oblong slot 56. Frame 50 includes side wings 50a and 50b which assist in guiding slide 52 and in turn in guiding extension 57 through slots 54 and 55. The entirety of the slide latch assembly in an exploded view form is illustrated in FIG. 7.

By means of clamping pressure applied against the lid 22 onto tray 21 the convex shape of each clip 51 will flatten in a spring-biased manner allowing the enlarged head 58 of each pin 53a and the enlarged diameter portion of collar 53 to fit into the enlarged end opening of each corresponding keyhole slot 31 and 32. Then by pushing or pulling the slides 52 (note in the same direction), the enlarged heads 58 and enlarged diameter portions will be received and retained by the narrower portions of each keyhole slot. The spring-biased nature of clip 51 which is still flattened from its normal convex shape, provides a continuous spring force which securely holds the tray and lid combination together in a closed condition without allowing any movement, vibration or looseness to these two main members. This enables the tray and lid combination of enclosure 20 to be secure and quiet. Even the action of the slide latch 49 is smooth and quiet and easily manipulated. By the user holding the tray and lid tightly together the clips 51 will be flattened and the convex slide can move almost effortlessly through the corresponding keyhole slots from the enlarged end which initially receives each of the heads 58 and enlarged diameter portions of the collars 53 into the narrower slot portion which securely holds the heads into position. Once each slide is pulled into its locking position the clamping force on the tray and lid which has been manually exerted can now be removed. This closing process is then reversed in order to open the enclosure. However, even if the tray and lid are not manually clamped together when manipulating the slot latches, they will still perform and function in the fashion described. There will simply be more force required because the pushing or pulling slide action will be required to flatten out each clip 51 as opposed to manually flattening those clips prior to moving the pins by holding the lid and tray together. However, even if the tray and lid are not manually clamped together the slide latch action will still be quiet and secure. The opposite ends of frame 50 are marked with the initials "OP" for open and "LK" for locked.

Referring to FIG. 6 another feature of the present invention is illustrated. It is to be noted that ribs 33 are spaced-apart slightly wider than the spacing of ribs 41 and 42, though the clearance is still close. These two pairs of ribs are also substantially parallel to each other. Further, the length of ribs 33 is just slightly less than the length of areas 40a and 40c. These dimensional and positional relationships permit the tray to be stacked on top of the lid. While this stacked arrangement is not locked nor rigidly secured, the tray is clearly retained in the lid such that normal forces which may be exerted on one of the two stacked enclosures will not allow one enclosure to separate from the other enclosure. The base of the tray stacks down onto and within the top of the lid and creates a securely stacked combination. Forces that try to push or pull the tray in a horizontal plane will result in the ribs 33 abutting up against either ribs 41 and 42 and/or the inside wall surface of frame portion 40. As a consequence of this design, a number of enclosures 20 can be stacked one on top of the other thereby providing a more convenient and efficient design over autoclave enclosures that are not stackable.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A plastic autoclave enclosure for receipt and storage of medical appliances and equipment comprising:
   a unitary, molded tray including a base panel, four sidewalls and an upper, generally rectangular, peripheral flange including a peripheral down turned lip, said base panel including a first pair of spaced-apart, stiffening and support ribs projecting downwardly from said base panel;
   a unitary, molded lid including a top surface central panel and an outwardly extending, peripheral flange including an outer peripheral down turned lip, the peripheral flange of said lid being sized and shaped to fit down over the peripheral flange and around the peripheral lip of said tray, said central panel including a generally rectangular raised frame having a second pair of spaced-apart, stiffening ribs which are substantially parallel and extend across said frame so as to divide said central panel into three recessed areas, wherein the size and spacing of said first pair of spaced-apart stiffening and support ribs of said base panel cooperate such that the ribs of said base panel fit in one or more of said three recessed areas in said lid;
   wherein the peripheral flange of said tray includes a pair of oppositely disposed tray ends, each of said tray ends defining a keyhold slot and wherein the upper peripheral flange of said lid includes a pair of oppositely disposed lid ends, each of said lid ends including a spring clip and slide latch with an enlarged-head fastener, the secured attachment of said lid to said tray being by way of the receipt of each said enlarged-head fasteners within a corresponding one of said keyhole slots; and
   wherein the flange of said tray includes a plurality of spaced-apart and raised protuberances, the height of the protuberances creating a separation between the lid and tray when the lid is placed on the tray, wherein the protuberances and slide latches are dimensioned so as to force the lid to flex when the slide latches are secured in the keyhole slots.

2. The plastic autoclave enclosure of claim 1 wherein said first pair of ribs in said base panel are dimensionally separated at a distance which is sufficient to span said second pair of ribs in said lid in a substantially parallel direction such that in a stacked configuration of a tray onto a lid, abutment of the firs and second pairs of ribs against each other limits tray to lid relative movement 3. A plastic autoclave enclosure for receipt and storage of medical appliances and equipment comprising:
   a unitary, molded tray including a base panel, four sidewalls and an upper, generally rectangular, peripheral flange including a peripheral down turned lip, said base panel including a first pair of spaced-apart, stiffening and support ribs projecting downwardly from said base panel;
   a unitary, molded lid including a top surface central panel and an outwardly extending, peripheral flange including an outer peripheral down turned lip, the peripheral flange of said lid being sized and shaped to fit down over the peripheral flange and around the peripheral lip of said tray, said central panel including a generally rectangular raised frame having a second pair of spaced-apart, stiffening ribs which are substantially parallel and extend across said frame so as to divide said central panel into three recessed areas, wherein the size and spacing of said first pair of spaced-apart stiffening and support ribs of said base panel cooperate with said lid for said tray to be stacked into said lid such that the ribs of said base panel fit in one or more of said three recessed areas in said lid;
   wherein said enclosure includes a pair of oppositely disposed slide latches attached to said lid and cooperating with said tray so as to securely attach the lid to the tray; and wherein the flange of said tray includes a plurality of spaced-apart and raised protuberances, the height of the protuberances creating a separation between the lid and tray when the lid is placed on the tray, wherein the protuberances and slide latches are dimensioned so as to force the lid to flex when the slide latches are secured.

4. The plastic autoclave enclosure of claim 3 wherein said first pair of ribs in said base panel are dimensionally separated at a distance which is sufficient to span said second pair of ribs in said lid in a substantially parallel direction such that in a a stacked configuration of a tray onto a lid, abutment of the first and second pairs of ribs against each other limits tray to lid relative movement.

5. A stackable autoclave enclosure comprising:
a tray having a base panel, four surrounding sidewalls and an outer peripheral flange, said base panel including a first pair of spaced-apart stiffening and support ribs;
a lid having a central panel, defined by a raised frame, and an outer surrounding peripheral flange, said raised frame including a second pair of spaced-apart stiffening ribs which divide said central panel into three recessed pockets, said tray base panel being stackable onto said lid by means of the first pair of ribs in said base panel fitting down into one or more of said three recessed pockets so as to extend in a direction substantially parallel to the direction of said second pair of ribs;
wherein said enclosure includes a pair of oppositely disposed slide latches attached to said lid and cooperating with said tray so as to securely attach the lid to the tray; and wherein the flange of said tray includes a plurality of spaced-apart and raised protuberances, the height of the protuberances creating a separation between the lid and tray when the lid is placed on the tray, wherein the protuberances and slide latches are dimensioned so as to force the lid to flex when the slide latches are secured.

6. A plastic autoclave enclosure for receipt and storage of medical appliances and equipment comprising:
a unitary, molded tray including a base panel, four sidewalls and an upper, generally rectangular, peripheral flange including a peripheral down turned lip and a plurality of spaced-apart and raised protuberances projecting upwardly from said peripheral flange;
a unitary, molded lid including a top surface central panel and an outwardly extending, peripheral flange including an outer peripheral down turned lip, the peripheral flange of said lid being sized and shaped to fit down over the peripheral flange and around the peripheral lip of said tray, said raised protuberances creating a lid to tray separation; and
latch means for securing the lid and tray together, wherein latching of the lid to the tray requires flexing of said lid in the area of said latch means while the lid to tray separation is maintained by said raised protuberances.

7. The autoclave enclosure of claim 6 wherein said latch means includes a slide latch disposed at each opposite end of said lid and a corresponding and cooperating keyhole aperture defined by the flange of said tray.

* * * * *

UNITED STATES PATENT AND TRADEMARK OFFICE
CERTIFICATE OF CORRECTION

PATENT NO. : 5,281,400

DATED : January 25, 1994

INVENTOR(S) : Bernie B. Berry, Jr.

It is certified that error appears in the above-identified patent and that said Letters Patent is hereby corrected as shown below:

In column 6, line 15, please insert --with said lid for said tray to be stacked into said lid-- before "such".

Signed and Sealed this

Fourteenth Day of June, 1994

Attest:

BRUCE LEHMAN

Attesting Officer

Commissioner of Patents and Trademarks